United States Patent
Foster et al.

(10) Patent No.: US 9,327,069 B2
(45) Date of Patent: May 3, 2016

(54) METHODS AND SYSTEMS FOR TREATING A MEDICAL CONDITION BY PROMOTING NEURAL REMODELING WITHIN THE BRAIN

(75) Inventors: Allison M. Foster, Los Angeles, CA (US); Rafael Carbunaru, Studio City, CA (US); Kristen N. Jaax, Saugus, CA (US); Todd K. Whitehurst, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 2001 days.

(21) Appl. No.: 11/393,565

(22) Filed: Mar. 29, 2006

(65) Prior Publication Data

US 2006/0178709 A1 Aug. 10, 2006

Related U.S. Application Data

(63) Continuation-in-part of application No. 11/315,781, filed on Dec. 21, 2005, now abandoned.

(60) Provisional application No. 60/638,608, filed on Dec. 21, 2004.

(51) Int. Cl.
*A61N 1/05* (2006.01)
*A61M 5/142* (2006.01)
(Continued)

(52) U.S. Cl.
CPC ......... *A61M 5/14276* (2013.01); *A61N 1/3605* (2013.01); *A61M 2210/0693* (2013.01); *A61N 1/0529* (2013.01); *A61N 1/0531* (2013.01);
(Continued)

(58) Field of Classification Search
CPC . A61N 1/0529; A61N 1/0531; A61N 1/0534; A61N 1/36082
USPC .............................................. 607/45, 46, 116
See application file for complete search history.

(56) References Cited

U.S. PATENT DOCUMENTS

| 3,760,984 A | 9/1973 | Theeuwes |
| 3,845,770 A | 11/1974 | Theeuwes et al. |
| 3,916,899 A | 11/1975 | Theeuwes et al. |

(Continued)

FOREIGN PATENT DOCUMENTS

| WO | WO 01/82398 A1 | 1/2001 |
| WO | WO 03/005465 A1 | 1/2003 |

OTHER PUBLICATIONS

Non-Final Office Action received in U.S. Appl. No. 11/315,781; Jul. 28, 2008.
(Continued)

*Primary Examiner* — Christopher D Koharski
*Assistant Examiner* — Michael D Abreu
(74) *Attorney, Agent, or Firm* — Lowe Graham Jones PLLC; Bruce E. Black

(57) ABSTRACT

Methods of treating a medical condition include applying at least one stimulus to a stimulation site within the brain of a patient with an implanted stimulator in accordance with one or more stimulation parameters. The at least one stimulus is configured to promote neural remodeling within the brain of the patient. Systems for treating a medical condition include an implantable stimulator configured to apply at least one stimulus to a stimulation site within the brain of a patient in accordance with one or more stimulation parameters. The at least one stimulus is configured to promote neural remodeling within the brain of the patient.

9 Claims, 11 Drawing Sheets

(51) Int. Cl.
*A61N 1/36* (2006.01)
*A61N 1/372* (2006.01)

(52) U.S. Cl.
CPC .......... *A61N1/0534* (2013.01); *A61N 1/36082* (2013.01); *A61N 1/37205* (2013.01)

(56) References Cited

U.S. PATENT DOCUMENTS

| | | | |
|---|---|---|---|
| 3,923,426 | A | 12/1975 | Theeuwes |
| 3,987,790 | A | 10/1976 | Eckenhoff et al. |
| 3,995,631 | A | 12/1976 | Higuchi et al. |
| 4,016,880 | A | 4/1977 | Theeuwes et al. |
| 4,036,228 | A | 7/1977 | Theeuwes |
| 4,111,202 | A | 9/1978 | Theeuwes |
| 4,111,203 | A | 9/1978 | Theeuwes |
| 4,203,440 | A | 5/1980 | Theeuwes |
| 4,203,442 | A | 5/1980 | Michaels |
| 4,210,139 | A | 7/1980 | Higuchi |
| 4,327,725 | A | 5/1982 | Cortese et al. |
| 4,360,019 | A | 11/1982 | Portner et al. |
| 4,487,603 | A | 12/1984 | Harris |
| 4,528,265 | A * | 7/1985 | Becker .......... 424/654 |
| 4,562,751 | A | 1/1986 | Nason et al. |
| 4,627,850 | A | 12/1986 | Deters et al. |
| 4,678,408 | A | 7/1987 | Nason et al. |
| 4,685,903 | A | 8/1987 | Cable et al. |
| 4,692,147 | A | 9/1987 | Duggan |
| 4,725,852 | A | 2/1988 | Gamblin et al. |
| 4,865,845 | A | 9/1989 | Eckenhoff et al. |
| 5,057,318 | A | 10/1991 | Magruder et al. |
| 5,059,423 | A | 10/1991 | Magruder et al. |
| 5,080,653 | A | 1/1992 | Voss et al. |
| 5,097,122 | A | 3/1992 | Colman et al. |
| 5,112,614 | A | 5/1992 | Magruder et al. |
| 5,137,727 | A | 8/1992 | Eckenhoff |
| 5,193,539 | A | 3/1993 | Schulman et al. |
| 5,193,540 | A | 3/1993 | Schulman et al. |
| 5,234,692 | A | 8/1993 | Magruder et al. |
| 5,234,693 | A | 8/1993 | Magruder et al. |
| 5,312,439 | A | 5/1994 | Loeb |
| 5,501,703 | A | 3/1996 | Holsheimer |
| 5,728,396 | A | 3/1998 | Peery et al. |
| 5,920,835 | A | 7/1999 | Huzenlaub et al. |
| 5,938,688 | A | 8/1999 | Schiff |
| 6,016,449 | A | 1/2000 | Fischell et al. |
| 6,051,017 | A | 4/2000 | Loeb et al. |
| 6,052,624 | A | 4/2000 | Mann |
| 6,164,284 | A | 12/2000 | Schulman et al. |
| 6,167,311 | A | 12/2000 | Rezai |
| 6,185,452 | B1 | 2/2001 | Schulman et al. |
| 6,208,894 | B1 | 3/2001 | Schulman et al. |
| 6,214,032 | B1 | 4/2001 | Loeb et al. |
| 6,219,580 | B1 | 4/2001 | Faltys et al. |
| 6,272,382 | B1 | 8/2001 | Faltys et al. |
| 6,280,873 | B1 | 8/2001 | Tsukamoto |
| 6,308,101 | B1 | 10/2001 | Faltys et al. |
| 6,339,725 | B1 | 1/2002 | Naritoku et al. |
| 6,343,226 | B1 | 1/2002 | Sunde et al. |
| 6,368,315 | B1 | 4/2002 | Gillis et al. |
| 6,381,496 | B1 | 4/2002 | Meadows et al. |
| 6,458,171 | B1 | 10/2002 | Tsukamoto |
| 6,487,446 | B1 | 11/2002 | Hill et al. |
| 6,516,227 | B1 | 2/2003 | Meadows et al. |
| 6,539,263 | B1 | 3/2003 | Schiff et al. |
| 6,552,000 | B2 | 4/2003 | Van Kammen |
| 6,553,263 | B1 | 4/2003 | Meadows et al. |
| 6,620,151 | B2 | 9/2003 | Blischak et al. |
| 6,666,845 | B2 | 12/2003 | Hooper et al. |
| 6,740,072 | B2 | 5/2004 | Starkweather et al. |
| 6,760,626 | B1 | 7/2004 | Boveja |
| 6,770,067 | B2 | 8/2004 | Lorenzen et al. |
| 7,353,065 | B2 * | 4/2008 | Morrell .......... 607/45 |
| 7,562,751 | B2 | 7/2009 | Godshaw et al. |
| 2001/0046625 | A1 | 11/2001 | Ruth, II et al. |
| 2001/0053476 | A1 | 12/2001 | Ruth et al. |
| 2003/0088274 | A1 * | 5/2003 | Gliner et al. .......... 607/3 |
| 2003/0181954 | A1 | 9/2003 | Rezai |
| 2003/0224074 | A1 * | 12/2003 | Choe et al. .......... 424/741 |
| 2005/0113882 | A1 | 5/2005 | Cameron et al. |
| 2005/0283201 | A1 | 12/2005 | Machado et al. |
| 2006/0247728 | A1 | 11/2006 | Foster et al. |
| 2007/0038264 | A1 | 2/2007 | Jaas et al. |
| 2010/0030287 | A1 | 2/2010 | Jaax et al. |

OTHER PUBLICATIONS

Office Action dated Apr. 15, 2009 in U.S. Appl. No. 11/315,781, filed Dec. 21, 2005, inventor: Kristen N. Jaax (8 pages).
Office Action dated Jun. 18, 2009 in U.S. Appl. No. 11/315,781, filed Dec. 21, 2005, inventor: Kristen N. Jaax, (11 pages).
Chang, Qiang, et al., Gap Junctional Communication Among Developing and Injured Motor Neurons, Brain Research Reviews, 32 (2000) 242-249.
Eisenberg, L., Experience, brain, and behavior: the importance of a head start. Pediatric 103(5 Pt 1):1031-1035.
Gubellini, Paolo, et al., Endogenous Neurotrophins are Required for the Induction of GABAegic Long-Term Potentiation in the Neonatal Rat Hippocampus, J. Neurosci, Jun. 15, 2005, 25(24):5796-5802.
Li, Ting Yu, et al., Plasticity of Rat Bone Marrow-Derived 5-Hydroxytryptamine-Sensitive Neurons: Dedifferentiation and Redifferentiation, Cell Biology International 28 (2004) 801-807.
Marks, Carolyn A., et al., Effects of Sleep Disruption on Rat Dentate Granule Cell LTP in Vivo, Brain Research Bulletin 66 (2005) 114-119.
Merzenich, Michael, Cognetive Neuroscience: Seeing in the Sound Zone, Nature 404(6780):820-1.
Palizvan, M.R., et al., Epileptogenic Insult Causes a Shift in the Form of Long-Term Potentiation Expression, Neuroscience 134 (2005) 415-423.
Stephens, David N., et al., Repeated Ethanol Exposure and Withdrawal Impairs Human Fear Conditioning and Depresses Long-Term Potentiation in Rat Amygdala and Hippocampus, Biol Psychiatry 2005; 58:392-400.
Sur, Mriganka, Cortical Specification: Microcircuits, Perceptual Identity, and an Overall Perspective, Perspectives on Developmental Neurobiology 1993, vol. 1, No. 2, pp. 109-113.
Vickers, M.H., et al., Neonatal Leptin Treatment Reverses Developmental Programming, Endocrinology 146 (10):4211-4216.
Walder, Sally et al., Up-regulation of Neural Stem Cell Markers Suggest the Occurence of Dedifferentiation in Regenerating Spinal Cord, Dev Genes Evol (2003) 213:625-630.
Zhang, Z., et al., Transdifferentiation of Neoplastic Cells, Medical Hypotheses (2001) 57(5), 635-666.
Zucchini, Silvia, et al., Alterations in Seizure Susceptibility and in Seizure-induced Plasticity after Pharmacologic and Genetic Manipulation of the Fibroblast Growth Factor-2 System, Epilepsia, 46(Suppl.5):52-58, 2005.
Final Office Action dated Mar. 14, 2011 in U.S. Appl. No. 11/478,827, filed Jun. 30, 2006, Inventor: Allison M. Foster, (7 pages).
Non-Final Office Action dated Oct. 5, 2010 in U.S. Appl. No. 11/478,827, filed Jun. 30, 2006, Inventor: Allison M. Foster, (19 pages).
Non-Final Office Action dated Dec. 23, 2010 in U.S. Appl. No. 12/575,974, filed Oct. 8, 2009, Inventor: Kristen N. Jaax, (16 pages).
Non-Final Office Action dated May 11, 2011 in U.S. Appl. No. 11/478,827, filed Jun. 30, 2006, Inventor: Allison M. Foster, (7 pages).
Final Office Action dated Nov. 8, 2011 in U.S. Appl. No. 11/478,827, filed Jun. 30, 2006, Inventor: Allison M. Foster, (11 pages).
Advisory Action dated Dec. 20, 2011 in U.S. Appl. No. 11/478,827, filed Jun. 30, 2006, Inventor: Allison M. Foster, (3 pages).
Final Office Action dated May 12, 2011 in U.S. Appl. No. 12/575,974, filed Oct. 8, 2009, Inventor: Kristen N. Jaax, (11 pages).
Advisory Action dated Aug. 17, 2011 in U.S. Appl. No. 12/575,974, filed Oct. 8, 2009, Inventor: Kristen N. Jaax, (10 pages).
Orrison, William, Atlas of brain function, cited in an Office Action dated Aug. 17, 2011 in U.S. Appl. No. 12/575,974, filed Oct. 8, 2009, Inventor: Kristen N. Jaax, (4 pages).

(56) References Cited

OTHER PUBLICATIONS

SE Koester and DD O'leary, Axon of early generated neurons in cingulate corter pioneer the corpus callosum, cited in an Office Action dated Aug. 17, 2011 in U.S. Appl. No. 12/575,974, filed Oct. 8, 2009, Inventor: Kristen N. Jaax, (2 pages).

Appeal Brief dated Oct. 12, 2011 in U.S. Appl. No. 12/575,974, filed Oct. 8, 2009, Inventor: Kristen N. Jaax, (12 pages).

* cited by examiner

METHODS AND SYSTEMS FOR TREATING A MEDICAL CONDITION BY PROMOTING NEURAL REMODELING WITHIN THE BRAIN

RELATED APPLICATIONS

The present application is a continuation-in-part application of U.S. application Ser. No. 11/315,781, filed Dec. 21, 2005, now abandoned which application claims the benefit of U.S. Provisional Application Ser. No. 60/638,608, filed Dec. 21, 2004. Both applications are incorporated herein by reference in their respective entireties.

BACKGROUND

Human behavior is intricately dependent on billions of neural connections within the brain. These neural connections are constantly altered and reorganized throughout the life of a human. For example, early in the embryonic and prenatal development of a human being, the cellular morphology of most neurons is characterized by an exuberant, massive outgrowth of dendrites and axons. This tangled network of neural structure allows for synaptic connections to be formed among many neural cells.

As the human being continues to develop, however, extensive reconstruction of the brain and spinal cord occurs. Programmed cell death decreases cell numbers by as much as fifty percent in some brain regions. Axonal and dendritic structures are pruned away and synaptic contacts are removed.

This second, regressive phase of neural development is driven by the interaction of the human being with its environment. For example, as a child acquires new skills, experience, knowledge, and behaviors, unused neural structures are pruned and removed while those that are used are further strengthened. Such activity-dependent changes in neural structure are reflected in tangible transformations visible in the brain's interior terrain.

It is believed that many disorders such as autism, schizophrenia, and depression result from an excess number of neural connections and/or faulty neural connections within the brain. It is likely that these excess and/or faulty neural connections are a result of mistakes made during the developmental establishment of neural connections.

SUMMARY

Methods of treating a medical condition include applying at least one stimulus to a stimulation site within the brain of a patient with an implanted stimulator in accordance with one or more stimulation parameters. The at least one stimulus is configured to promote neural remodeling within the brain of the patient.

Systems for treating a medical condition include an implantable stimulator configured to apply at least one stimulus to a stimulation site within the brain of a patient in accordance with one or more stimulation parameters. The at least one stimulus is configured to promote neural remodeling within the brain of the patient.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Methods and systems for treating a medical condition by promoting neural remodeling within the brain are described herein. As used herein and in the appended claims, unless otherwise specifically denoted, neural remodeling is the ability of neural circuits to undergo changes in function and/or organization. An implanted stimulator is configured to apply at least one stimulus to a stimulation site within the brain of a patient in accordance with one or more stimulation parameters. The stimulus is configured to promote neural remodeling and may include electrical stimulation, drug stimulation, gene infusion, chemical stimulation, thermal stimulation, electromagnetic stimulation, mechanical stimulation, and/or any other suitable stimulation.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1A:
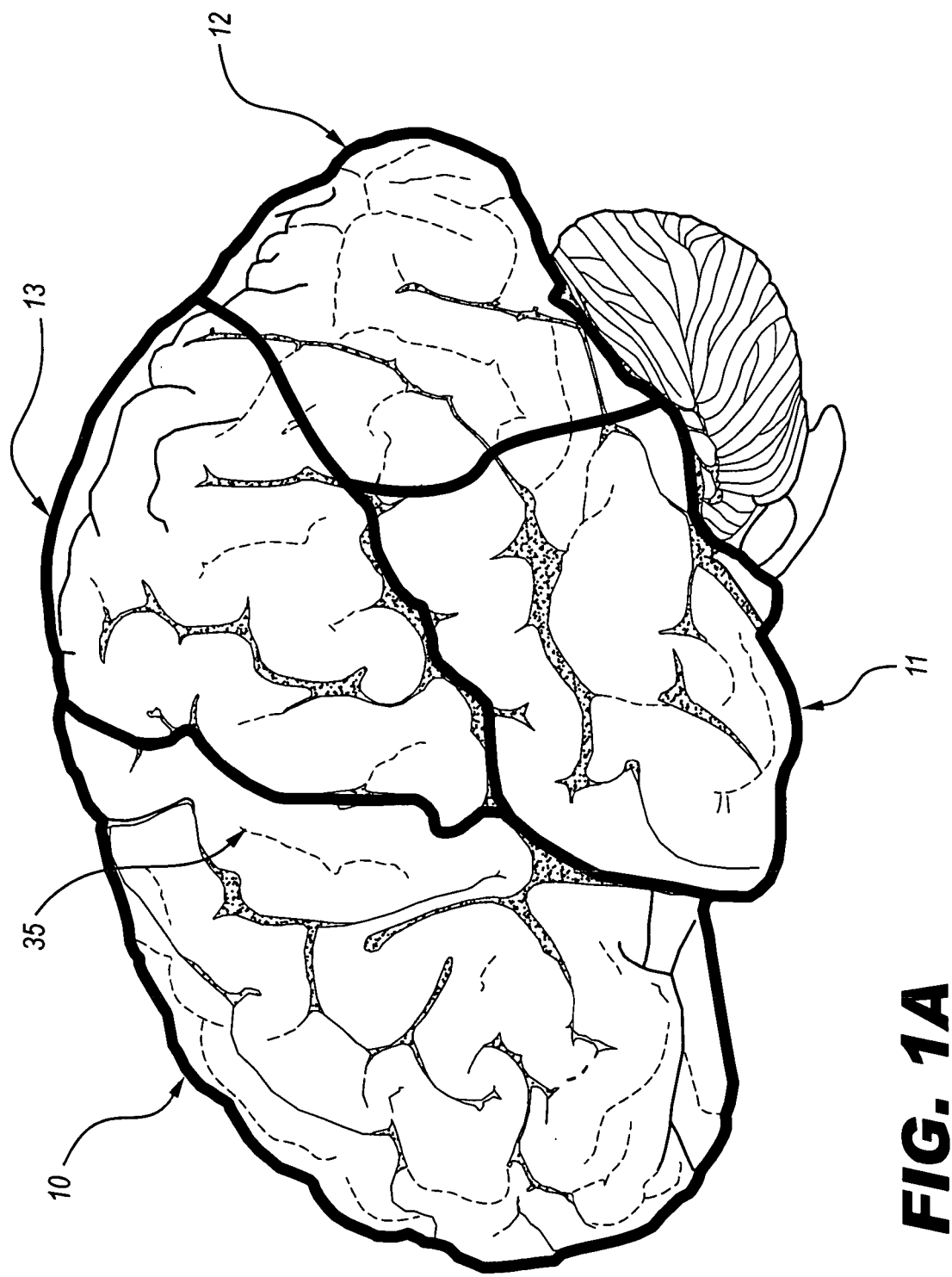
FIG. 1A depicts the lateral surface of the brain.

FIG. 1A depicts the lateral surface of the brain. As shown in FIG. 1A, the brain may be divided into a number of geographical lobes. The frontal lobe (10) is located at the front or anterior portion of the brain, the temporal lobes (11) are located on the sides or lateral portions of the brain, the occipital lobe (12) is located at the back or posterior of the brain, and the parietal lobe (13) is located at the top or superior portion of the brain toward the back or posterior half of the brain. Each lobe contains areas responsible for a number of different functions.

The cerebral cortex (35) is the outermost layer of the brain and is involved in many complex brain functions including, but not limited to, memory, attention, perceptual awareness, thinking, language, and consciousness. The surface layer of the cerebral cortex (35) is called the neocortex. The neocortex is the most highly developed portion of the human brain and is believed to be involved with higher mental processes including, but not limited to, planning, reasoning, and problem solving. It is also believed that the neocortex is linked to self-awareness and consciousness.

Figure 1B:
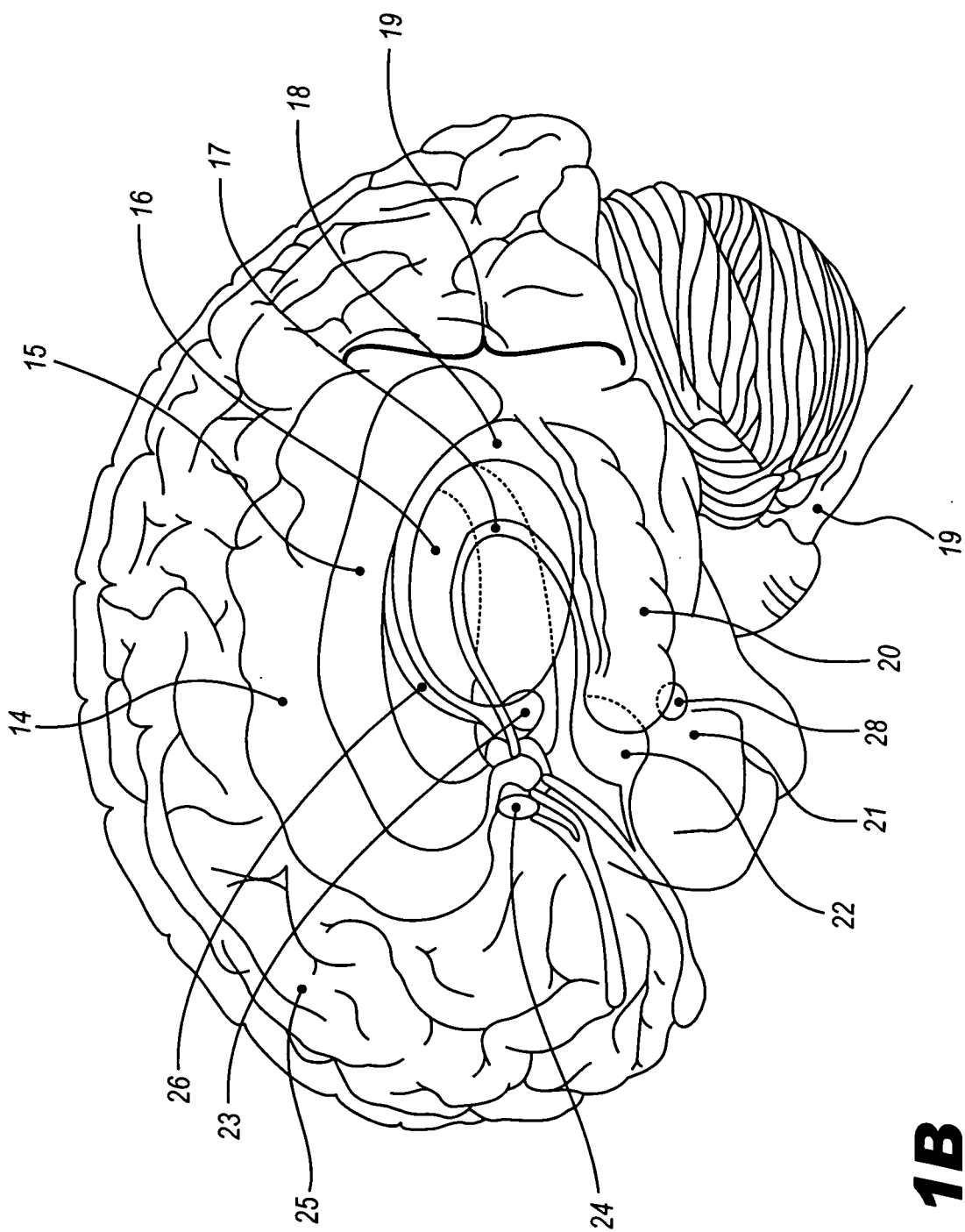
FIG. 1B is a perspective lateral view of the brain.

FIG. 1B is a perspective lateral view of the brain and depicts various structures of the limbic system. The limbic system is involved with emotion, learning, and memory. As shown in FIG. 1B, the limbic system includes several subcortical structures such as, but not limited to, the cingulate gyrus (14), corpus collosum (15), thalamus (16), stria terminalis (17), caudate nucleus (18), basal ganglia (19), hippocampus (20), entorhinal cortex (21), amygdala (22), mammillary body (23), medial septal nucleus (24), prefrontal cortex (25), and fornix (26).

FIG. 1B also shows the pituitary gland (28) and brainstem (29). The pituitary gland (28) is a small gland located at the base of the brain that secretes several different hormones involved in key metabolic processes throughout the body. The brainstem (29) is the part of the central nervous system that houses the nerve centers of the head as well as the centers for respiration and heart control. The brainstem extends from the base of the brain to the spinal cord.

Figure 1C:
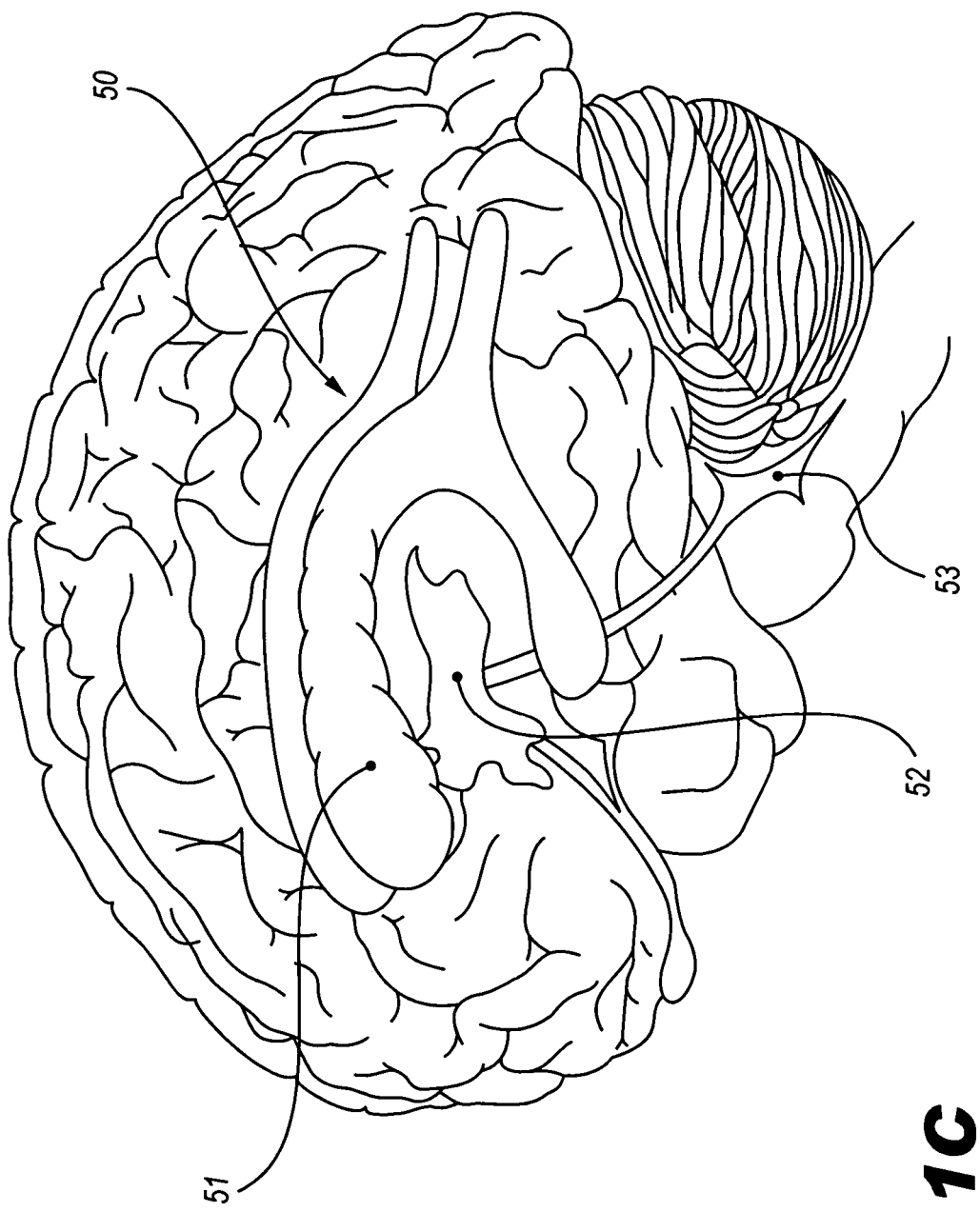
FIG. 1C is another perspective lateral view of the brain and shows the cerebral ventricles.

FIG. 1C is another perspective lateral view of the brain and shows the cerebral ventricles (50). The cerebral ventricles (50) include paired lateral ventricles (51), the third ventricle (52), and the fourth ventricle (53). Each of these cerebral ventricles (50) is filled with cerebrospinal fluid, which is a clear bodily fluid. The cerebrospinal fluid has many functions, one of which is to act as a cushion or buffer for the cerebral cortex (35; FIG. 1A).

Figure 1D:
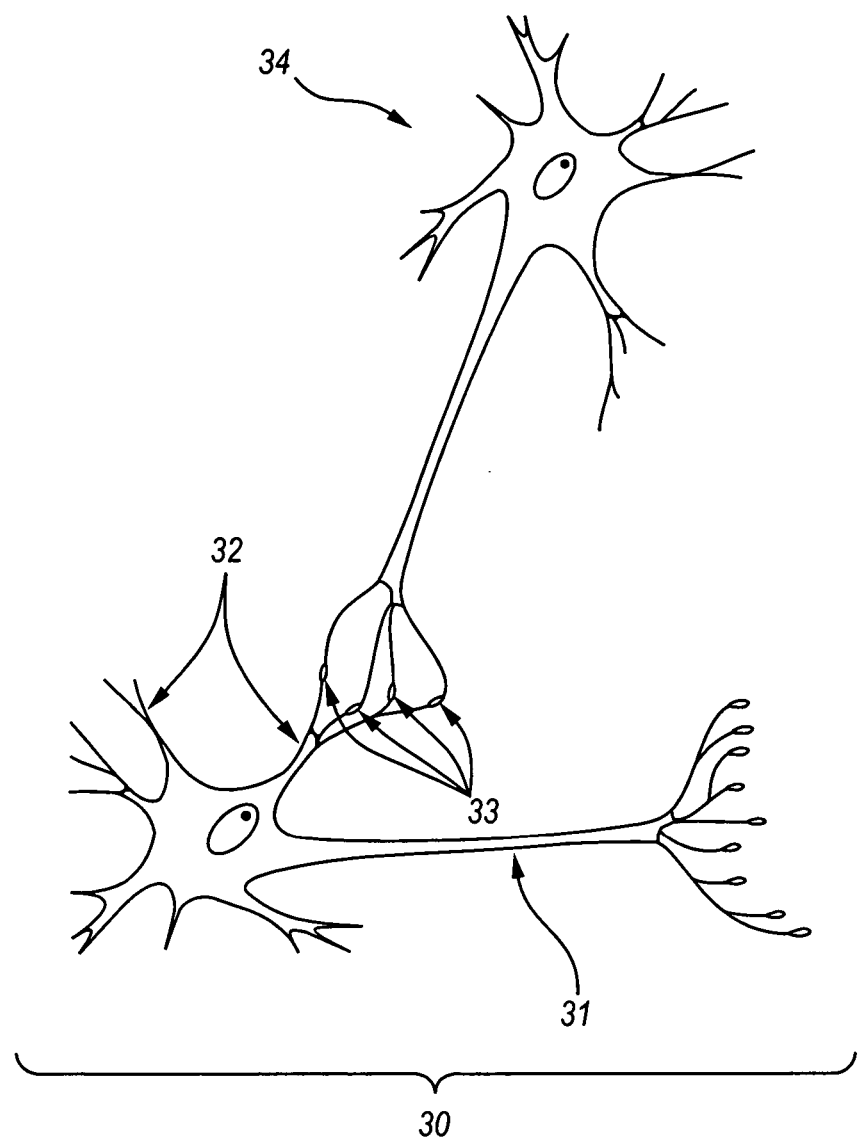
FIG. 1D illustrates an exemplary neuron.

The brain also includes millions of neurons that innervate its various parts. FIG. 1D illustrates an exemplary neuron (30). As shown in FIG. 1D, a neuron (30) includes an axon (31) and a number of dendrites (32). The axon (31) is the long, thread-like part of the nerve cell that extends from the cell body and is configured to transmit nerve impulses to other neurons or to other structures within the patient (e.g., various portions of the brain). Dendrites (32) are the tree-like extensions of the neuron (30), as illustrated in FIG. 1D, and are configured to form synaptic contacts (33) with the terminals of other nerve cells (e.g., 34) to allow nerve impulses to be transmitted.

Synaptic contacts (33), also called synapses, are specialized junctions through which neurons signal to one another and to non-neuronal cells, such as the various areas in the brain as described in connection with FIGS. 1A-1C. Synapses (33) allow neurons to form interconnected neural circuits and are thus vital to the biological computations that underlie perception and thought. Synapses (33) also allow the nervous system to connect to and control the other systems of the body.

As mentioned, axons (31), dendrites (32), and synapses (33) that are no longer used as a person develops are normally removed by the person's nervous system—a process know as developmental or neural pruning. However, when developmental pruning fails to function normally, excess neural connections may produce aberrant synaptic weighting and global disruption of function within the brain. Moreover, it is believed that, within such an overabundance of neural connections due to a lack of developmental pruning, many of the neural connections will be faulty. Synaptic weighting is a measure of the strength of the connection between a pre-synaptic neuron's terminals and the post-synaptic neuron's dendrites. A synaptic connection with a larger weight value have a stronger post-synaptic effect than a connection with low weight. A weight of zero between the terminals of a first neuron and the dendrites of a second neuron indicates that the neurotransmitters released by the terminals of the first have no effect on the dendrites of the second. A large positive value is usually associated with an excitatory connection, while a negative value with is associated with an inhibitory connection.

Many medical conditions have been linked to faulty neural connections and/or abnormal developmental pruning of axons, dendrites, and synapses within the brain. Such medical conditions include, but are not limited to, autism, psychological disorders (e.g., schizophrenia, compulsive behaviors, and depression), neurodegenerative diseases (e.g., Huntington's disease, Alzheimer's disease, and amyotrophic lateral sclerosis), and chromosomal abnormalities (e.g., Down syndrome and Klinefelter syndrome). For example, postmortem examinations of autistic human brains show abnormally small, densely packed cells in many areas of the brain including, but not limited to, those illustrated in FIGS. 1A-1C. Abnormally small, densely packed cells suggest that normal neural development, particularly developmental pruning, has been curtailed.

Nearly every brain area has been implicated in the disorders listed above. In particular, it is believed that faulty neural connections and/or abnormal developmental pruning of neural structures within the temporal lobe, limbic system, pituitary gland, brainstem, cerebral cortex, and/or any other midbrain structure are at least in part responsible for the deficits of one or more of the disorders listed above.

Hence, it is believed that a number of different medical conditions may be treated by promoting neural remodeling to remove and/or repair faulty neural connections in the brain. As used herein and in the appended claims, unless otherwise specifically denoted, neural remodeling is the ability of neural circuits to undergo changes in function and/or organization. The medical conditions that may be treated by promoting neural remodeling within the brain include, but are not limited to, autism, psychological disorders (e.g., schizophrenia, compulsive behaviors, and depression), neurodegenerative diseases (e.g., Huntington's disease, Alzheimer's disease, and amyotrophic lateral sclerosis), and chromosomal abnormalities (e.g., Down syndrome and Klinefelter syndrome), bad habits (e.g., smoking or overeating), traumatic brain injuries (e.g., stroke), and any pathological consequence thereof.

In some examples, as will be explained in more detail below, neural remodeling may be induced by applying a stimulus to one or more areas of the brain. The stimulus may include an electrical stimulation current, one or more drugs, gene infusion, chemical stimulation, thermal stimulation, electromagnetic stimulation, mechanical stimulation, and/or any other suitable stimulus. The stimulus is configured to cause neural structures within the brain to revert back to a juvenile neural phenotype. Developmental events may then recur naturally or with the aid of stimuli, thereby allowing a normal adult phenotype to be established with properly formed neural connections.

Consequently, as will be described in more detail below, a stimulator may be implanted within a patient and configured to deliver a stimulus to one or more stimulation sites within the brain to promote neural remodeling within the brain. As used herein and in the appended claims, unless otherwise specifically denoted, "promoting" neural remodeling refers to inducing neural dedifferentiation and/or assisting in the redifferentiation process in which neural connections are reformed.

As used herein, and in the appended claims, the term "stimulator" will be used broadly to refer to any device that delivers a stimulus, such as an electrical stimulation current, one or more drugs, or other chemical stimulation, thermal stimulation, electromagnetic stimulation, mechanical stimulation, gene infusion, and/or any other suitable stimulation at a stimulation site to promote neural remodeling. Thus, the term "stimulator" includes, but is not limited to, a stimulator, microstimulator, implantable pulse generator (IPG), system control unit, cochlear implant, deep brain stimulator, drug pump, or similar device.

The stimulation site referred to herein may include any area within the brain. For example, the stimulation site may include one or more of the following locations within the brain: any area within, on, or in the vicinity of the temporal lobe, limbic system, pituitary gland, brainstem, cerebral cortex, and/or other midbrain structure. The stimulation site may additionally or alternatively include a cerebral ventricle and/or any area in the frontal lobe, occipital lobe, or parietal lobe.

Figure 2:
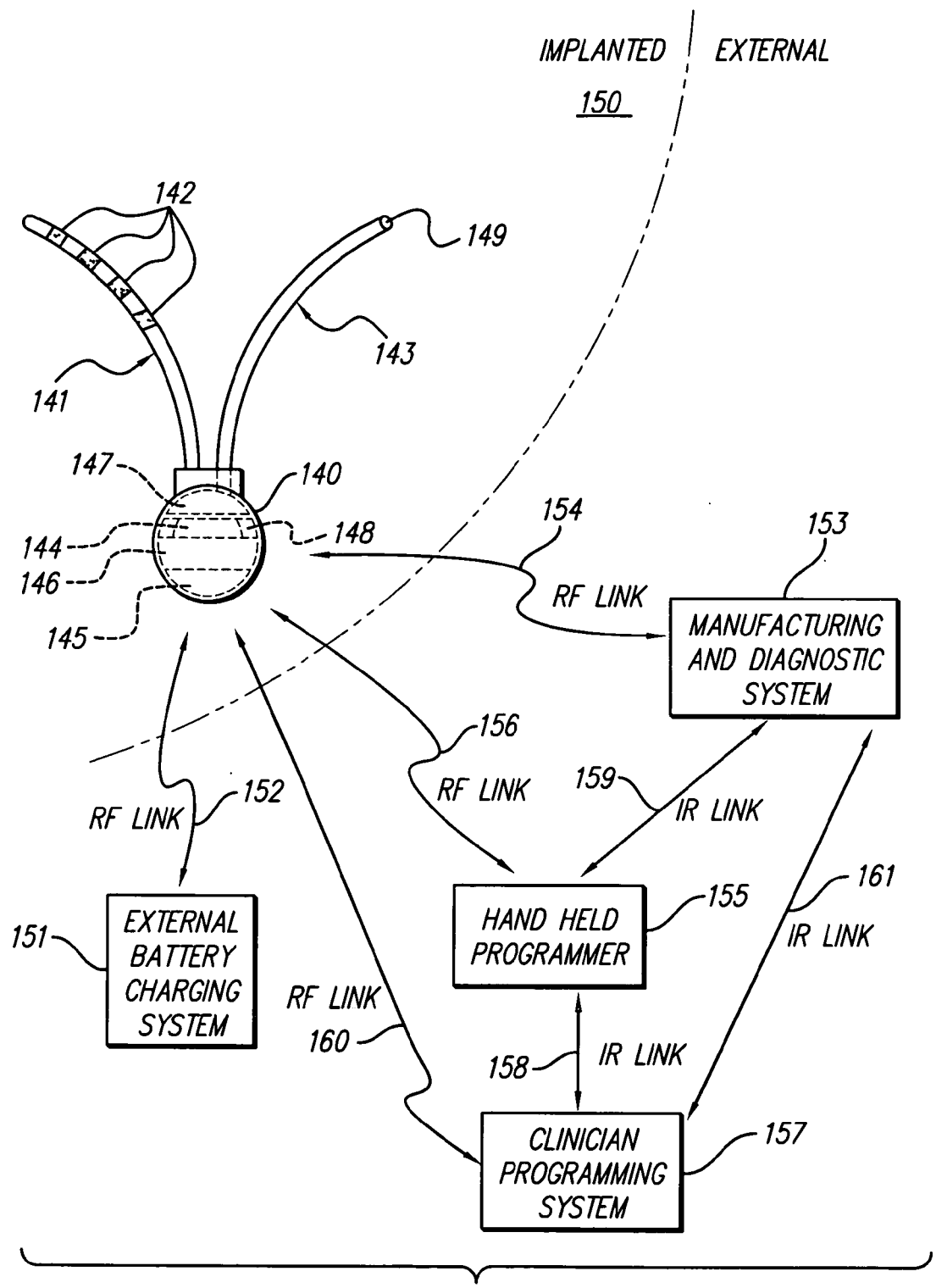
FIG. 2 illustrates an exemplary stimulator that may be used to apply a stimulus to a stimulation site within a patient to promote neural remodeling according to principles described herein.

To facilitate an understanding of the methods of optimally promoting neural remodeling to treat a medical condition, a more detailed description of the stimulator and its operation will now be given with reference to the figures. FIG. 2 illustrates an exemplary stimulator (140) that may be implanted within a patient (150) and used to apply a stimulus to a stimulation site, e.g., an electrical stimulation of the stimulation site, an infusion of one or more drugs at the stimulation site, or both. The electrical stimulation function of the stimulator (140) will be described first, followed by an explanation of the possible drug delivery function of the stimulator (140). It will be understood, however, that the stimulator (140) may be configured to provide only electrical stimulation, only a drug stimulation, both types of stimulation or any other type of stimulation as best suits a particular patient.

The exemplary stimulator (140) shown in FIG. 2 is configured to provide electrical stimulation to a stimulation site within a patient and may include a lead (141) having a proximal end coupled to the body of the stimulator (140). The lead (141) also includes a number of electrodes (142) configured to apply an electrical stimulation current to a stimulation site. The lead (141) may include any number of electrodes (142) as best serves a particular application. The electrodes (142) may be arranged as an array, for example, having at least two or at least four collinear electrodes. In some embodiments, the electrodes are alternatively inductively coupled to the stimulator (140). The lead (141) may be thin (e.g., less than 3 millimeters in diameter) such that the lead (141) may be positioned near a stimulation site. In some alternative examples, as will be illustrated in connection with FIG. 3, the stimulator (140) is leadless.

As illustrated in FIG. 2, the stimulator (140) includes a number of components. It will be recognized that the stimulator (140) may include additional or alternative components as best serves a particular application. A power source (145) is configured to output voltage used to supply the various components within the stimulator (140) with power and/or to generate the power used for electrical stimulation. The power source (145) may be a primary battery, a rechargeable battery, super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like. Alternatively, the stimulator (140) may include one or more components configured to receive power from another medical device that is implanted within the patient.

When the power source (145) is a battery, it may be a lithium-ion battery or other suitable type of battery. When the power source (145) is a rechargeable battery, it may be recharged from an external system through a power link such as a radio frequency (RF) power link. One type of rechargeable battery that may be used is described in International Publication WO 01/82398 A1, published Nov. 1, 2001, and/or WO 03/005465 A1, published Jan. 16, 2003, both of which are incorporated herein by reference in their respective entireties. Other battery construction techniques that may be used to make a power source (145) include those shown, e.g., in U.S. Pat. Nos. 6,280,873; 6,458,171, and U.S. Publications 2001/0046625 A1 and 2001/0053476 A1, all of which are incorporated herein by reference in their respective entireties. Recharging can be performed using an external charger.

The stimulator (140) may also include a coil (148) configured to receive and/or emit a magnetic field (also referred to as a radio frequency (RF) field) that is used to communicate with, or receive power from, one or more external devices (151, 153, 155). Such communication and/or power transfer may include, but is not limited to, transcutaneously receiving data from the external device, transmitting data to the external device, and/or receiving power used to recharge the power source (145).

For example, an external battery charging system (EBCS) (151) may provide power used to recharge the power source (145) via an RF link (152). External devices including, but not limited to, a hand held programmer (HHP) (155), clinician programming system (CPS) (157), and/or a manufacturing and diagnostic system (MDS) (153) may be configured to activate, deactivate, program, and test the stimulator (140) via one or more RF links (154, 156). It will be recognized that the links, which are RF links (152, 154, 156) in the illustrated example, may be any type of link used to transmit data or energy, such as an optical link, a thermal link, or any other energy-coupling link. One or more of these external devices (153, 155, 157) may also be used to control the infusion of one or more drugs into the stimulation site.

Additionally, if multiple external devices are used in the treatment of a patient, there may be some communication among those external devices, as well as with the implanted stimulator (140). Again, any type of link for transmitting data or energy may be used among the various devices illustrated. For example, the CPS (157) may communicate with the HHP (155) via an infrared (IR) link (158), with the MDS (153) via an IR link (161), and/or directly with the stimulator (140) via an RF link (160). As indicated, these communication links (158, 161, 160) are not necessarily limited to IR and RF links and may include any other type of communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the stimulator (140). Furthermore, it will be recognized that the functions performed by any two or more of the HHP (155), MDS (153), CPS (157), and EBCS (151) may be performed by a single external device. One or more of the external devices (153, 155, 157) may be embedded in a seat cushion, mattress cover, pillow, garment, belt, strap, pouch, or the like so as to be positioned near the implanted stimulator (140) when in use.

The stimulator (140) may also include electrical circuitry (144) configured to produce electrical stimulation pulses that are delivered to the stimulation site via the electrodes (142). In some embodiments, the stimulator (140) may be configured to produce monopolar stimulation. The stimulator (140) may alternatively or additionally be configured to produce multipolar stimulation including, but not limited to, bipolar or tripolar stimulation.

The electrical circuitry (144) may include one or more processors configured to decode stimulation parameters and generate the stimulation pulses. In some embodiments, the stimulator (140) has at least four channels and drives up to sixteen electrodes or more. The electrical circuitry (144) may include additional circuitry such as capacitors, integrated circuits, resistors, coils, and the like configured to perform a variety of functions as best serves a particular application.

The stimulator (140) may also include a programmable memory unit (146) for storing one or more sets of data and/or stimulation parameters. The stimulation parameters may include, but are not limited to, electrical stimulation parameters, drug stimulation parameters, and other types of stimulation parameters. The programmable memory (146) allows a patient, clinician, or other user of the stimulator (140) to adjust the stimulation parameters such that the stimulation applied by the stimulator (140) is safe and efficacious for treatment of a particular patient. The different types of stimulation parameters (e.g., electrical stimulation parameters and drug stimulation parameters) may be controlled independently. However, in some instances, the different types of stimulation parameters are coupled. For example, electrical stimulation may be programmed to occur only during drug stimulation or vice versa. Alternatively, the different types of stimulation may be applied at different times or with only some overlap. The programmable memory (146) may be any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, waveform (e.g., square or sinusoidal), electrode configuration (i.e., anode-cathode assignment), burst pattern (e.g., burst on time and burst off time), duty cycle or burst repeat interval, ramp on time, and ramp off time of the stimulation current that is applied to the stimulation site. The drug stimulation parameters may control various parameters including, but not limited to, the amount of drugs infused at the stimulation site, the rate of drug infusion, and the frequency of drug infusion. For example, the drug stimulation parameters may cause the drug infusion rate to be intermittent, constant, or bolus. Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

Specific stimulation parameters may have different effects on different stimulation sites and/or different patients. Thus, in some embodiments, the stimulation parameters may be adjusted by the patient, a clinician, or other user of the stimulator (140) as best serves the particular stimulation site or patient being treated. The stimulation parameters may also be automatically adjusted by the stimulator (140), as will be described below. For example, the stimulator (140) may increase excitement of neural tissue to induce neural remodeling, for example, by applying a stimulation current having a relatively low frequency (e.g., less than 100 Hz). The stimulator (140) may also decrease excitement of neural tissue to assist in dedifferentiation of the neural tissue by applying a relatively high frequency (e.g., greater than 100 Hz). The stimulator (140) may also, or alternatively, be programmed to apply the stimulation current to a stimulation site intermittently or continuously.

Additionally, the exemplary stimulator (140) shown in FIG. 2 is configured to promote neural remodeling by applying one or more drugs at a stimulation site within the brain of a patient. For this purpose, a pump (147) may also be included within the stimulator (140). The pump (147) is configured to store and dispense one or more drugs, for example, through a catheter (143). The catheter (143) is coupled at a proximal end to the stimulator (140) and may have an infusion outlet (149) for infusing dosages of the one or more drugs at the stimulation site. In some embodiments, the stimulator (140) may include multiple catheters (143) and/or pumps (147) for storing and infusing dosages of the one or more drugs at the stimulation site.

The pump (147) or controlled drug release device described herein may include any of a variety of different drug delivery systems. Controlled drug release devices based upon a mechanical or electromechanical infusion pump may be used. In other examples, the controlled drug release device can include a diffusion-based delivery system, e.g., erosion-based delivery systems (e.g., a polymer impregnated with one or more drugs placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps. Another example is a micro-drug pump.

Exemplary pumps (147) or controlled drug release devices suitable for use as described herein include, but are not necessarily limited to, those disclosed in U.S. Pat. Nos. 3,760, 984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. Additional exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Exemplary micro-drug pumps suitable for use as described herein include, but are not necessarily limited to, those disclosed in U.S. Pat. Nos. 5,234, 692; 5,234,693; 5,728,396; 6,368,315; 6,666,845; and 6,620, 151. All of these listed patents are incorporated herein by reference in their respective entireties.

The one or more drugs that may be applied to a stimulation site to promote neural remodeling may have an excitatory effect on the stimulation site. Additionally or alternatively, the one or more drugs may have an inhibitory effect on the stimulation site to promote neural remodeling. Exemplary excitatory drugs that may be applied to a stimulation site to promote neural remodeling include, but are not limited to, at least one or more of the following: an excitatory neurotransmitter (e.g., glutamate, dopamine, norepinephrine, epinephrine, acetylcholine, serotonin); an excitatory neurotransmitter agonist (e.g., glutamate receptor agonist, L-aspartic acid, N-methyl-D-aspartic acid (NMDA), bethanechol, norepinephrine); an inhibitory neurotransmitter antagonist(s) (e.g., bicuculline); an agent that increases the level of an excitatory neurotransmitter (e.g., edrophonium, Mestinon); and/or an agent that decreases the level of an inhibitory neurotransmitter (e.g., bicuculline).

Exemplary inhibitory drugs that may be applied to a stimulation site to promote neural remodeling include, but are not limited to, at least one or more of the following: an inhibitory neurotransmitter(s) (e.g., gamma-aminobutyric acid, a.k.a. GABA, dopamine, glycine); an agonist of an inhibitory neurotransmitter (e.g., a GABA receptor agonist such as midazolam or clondine, muscimol); an excitatory neurotransmitter antagonist(s) (e.g. prazosin, metoprolol, atropine, benztropine); an agent that increases the level of an inhibitory neurotransmitter; an agent that decreases the level of an excitatory neurotransmitter (e.g., acetylcholinesterase, Group II metabotropic glutamate receptor (mGluR) agonists such as DCG-IV); a local anesthetic agent (e.g., lidocaine); and/or an analgesic medication. It will be understood that some of these drugs, such as dopamine, may act as excitatory neurotransmitters in some stimulation sites and circumstances, and as inhibitory neurotransmitters in other stimulation sites and circumstances.

Additional or alternative drugs that may be applied to a stimulation site to promote neural remodeling include, but are not limited to, neurotrophic factors (e.g., brain derived neotrophic factors (BDNF) and glial cell line derived neurotrophic factors (GDNF)), fibroblast growth factors, ethanol, steroid hormones (e.g., testosterone), cannabinoids (e.g., $\Delta^9$-tetrahydrocannabinol), and/or any other drug listed herein. Injections of biologic or genetic material may promote neural remodeling through up or down-regulating proapoptotic genes and/or proteins of the Bcl-2 family such as Bax or Bid, up-regulating gap junction proteins, and/or up or down-regulating actin and microtubule proteins.

Any of the drugs listed above, alone or in combination, or other drugs or combinations of drugs developed or shown to promote neural remodeling may be applied to the stimulation site. In some embodiments, the one or more drugs are infused chronically into the stimulation site. Additionally or alternatively, the one or more drugs may be infused acutely into the stimulation site in response to a biological signal or a sensed need for the one or more drugs.

The stimulator (140) of FIG. 2 is illustrative of many types of stimulators that may be used to apply a stimulus to a stimulation site to promote neural remodeling. For example, the stimulator (140) may include an implantable pulse generator (IPG) coupled to one or more leads having a number of electrodes, a spinal cord stimulator (SCS), a cochlear implant, a deep brain stimulator, a drug pump (mentioned previously), a micro-drug pump (mentioned previously), or any other type of implantable stimulator configured to deliver a stimulus at a stimulation site within a patient. Exemplary IPGs suitable for use as described herein include, but are not limited to, those disclosed in U.S. Pat. Nos. 6,381,496, 6,553,263; and 6,760, 626. Exemplary spinal cord stimulators suitable for use as described herein include, but are not limited to, those disclosed in U.S. Pat. Nos. 5,501,703; 6,487,446; and 6,516,227. Exemplary cochlear implants suitable for use as described herein include, but are not limited to, those disclosed in U.S. Pat. Nos. 6,219,580; 6,272,382; and 6,308,101. Exemplary deep brain stimulators suitable for use as described herein include, but are not limited to, those disclosed in U.S. Pat. Nos. 5,938,688; 6,016,449; and 6,539,263. All of these listed patents are incorporated herein by reference in their respective entireties.

Alternatively, the stimulator (140) may include an implantable microstimulator, such as a BION® microstimulator (Advanced Bionics® Corporation, Valencia, Calif.). Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 3:
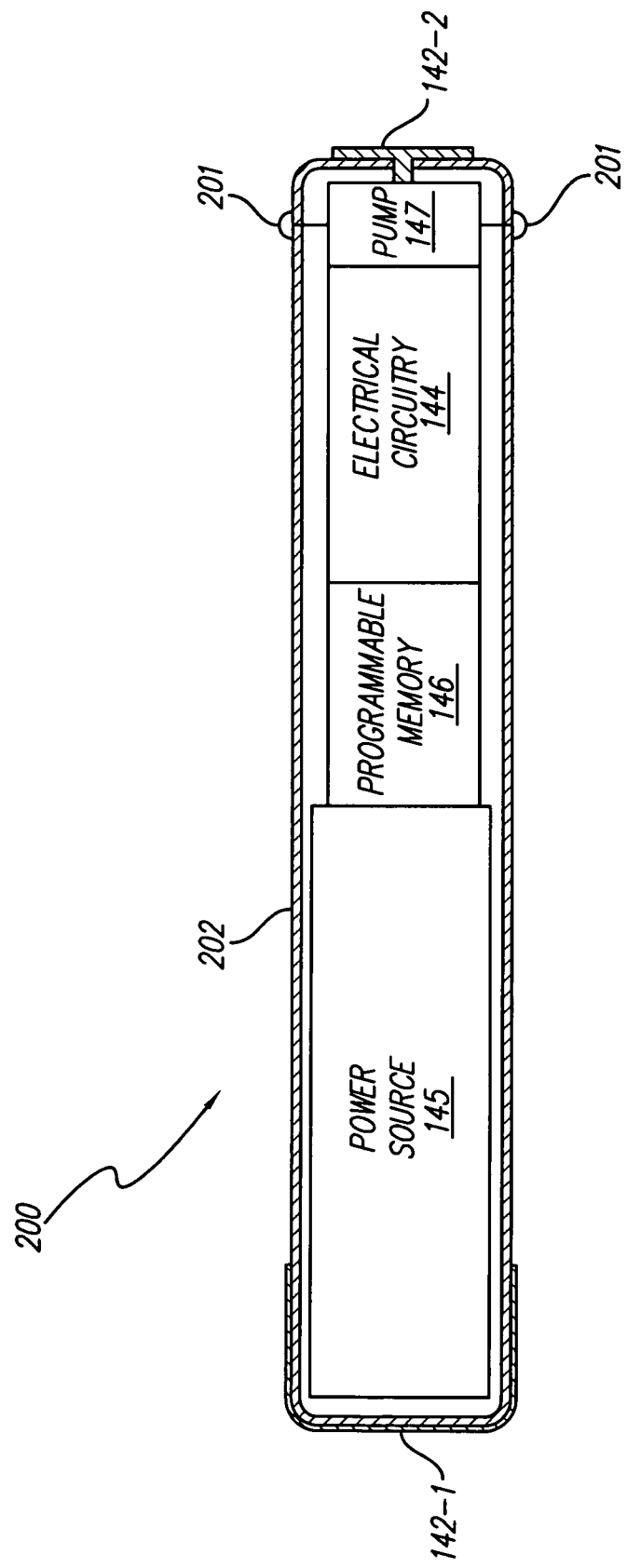
FIG. 3 illustrates an exemplary microstimulator that may be used as the stimulator according to principles described herein.

FIG. 3 illustrates an exemplary microstimulator (200) that may be used as the stimulator (140; FIG. 2) described herein. Other configurations of the microstimulator (200) are possible, as shown in the above-referenced patents and as described further below.

As shown in FIG. 3, the microstimulator (200) may include the power source (145), the programmable memory (146), the electrical circuitry (144), and the pump (147) described in connection with FIG. 2. These components are housed within a capsule (202). The capsule (202) may be a thin, elongated cylinder or any other shape as best serves a particular application. The shape of the capsule (202) may be determined by the structure of the desired target nerve, the surrounding area, and the method of implantation. In some embodiments, the volume of the capsule (202) is substantially equal to or less than three cubic centimeters. In some embodiments, the microstimulator (200) may include two or more leadless electrodes (142) disposed on the outer surface of the microstimulator (200).

The external surfaces of the microstimulator (200) may advantageously be composed of biocompatible materials. For example, the capsule (202) may be made of glass, ceramic, metal, or any other material that provides a hermetic package that will exclude water vapor but permit passage of electromagnetic fields used to transmit data and/or power. The electrodes (142) may be made of a noble or refractory metal or compound, such as platinum, iridium, tantalum, titanium, titanium nitride, niobium or alloys of any of these, in order to avoid corrosion or electrolysis which could damage the surrounding tissues and the device.

The microstimulator (200) may also include one or more infusion outlets (201). The infusion outlets (201) facilitate the infusion of one or more drugs at a stimulation site to promote neural remodeling. The infusion outlets (201) may dispense one or more drugs directly to the treatment site. Alternatively, catheters may be coupled to the infusion outlets (201) to deliver the drug therapy to a treatment site some distance from the body of the microstimulator (200). The stimulator (200) of FIG. 3 also includes electrodes (142-1 and 142-2) at either end of the capsule (202). One of the electrodes (142) may be designated as a stimulating electrode to be placed close to the treatment site and one of the electrodes (142) may be designated as an indifferent electrode used to complete a stimulation circuit.

The microstimulator (200) may be implanted within a patient with a surgical tool such as a hypodermic needle, bore needle, or any other tool specially designed for the purpose. Alternatively, the microstimulator (200) may be implanted using endoscopic or laparoscopic techniques.

Figure 4:
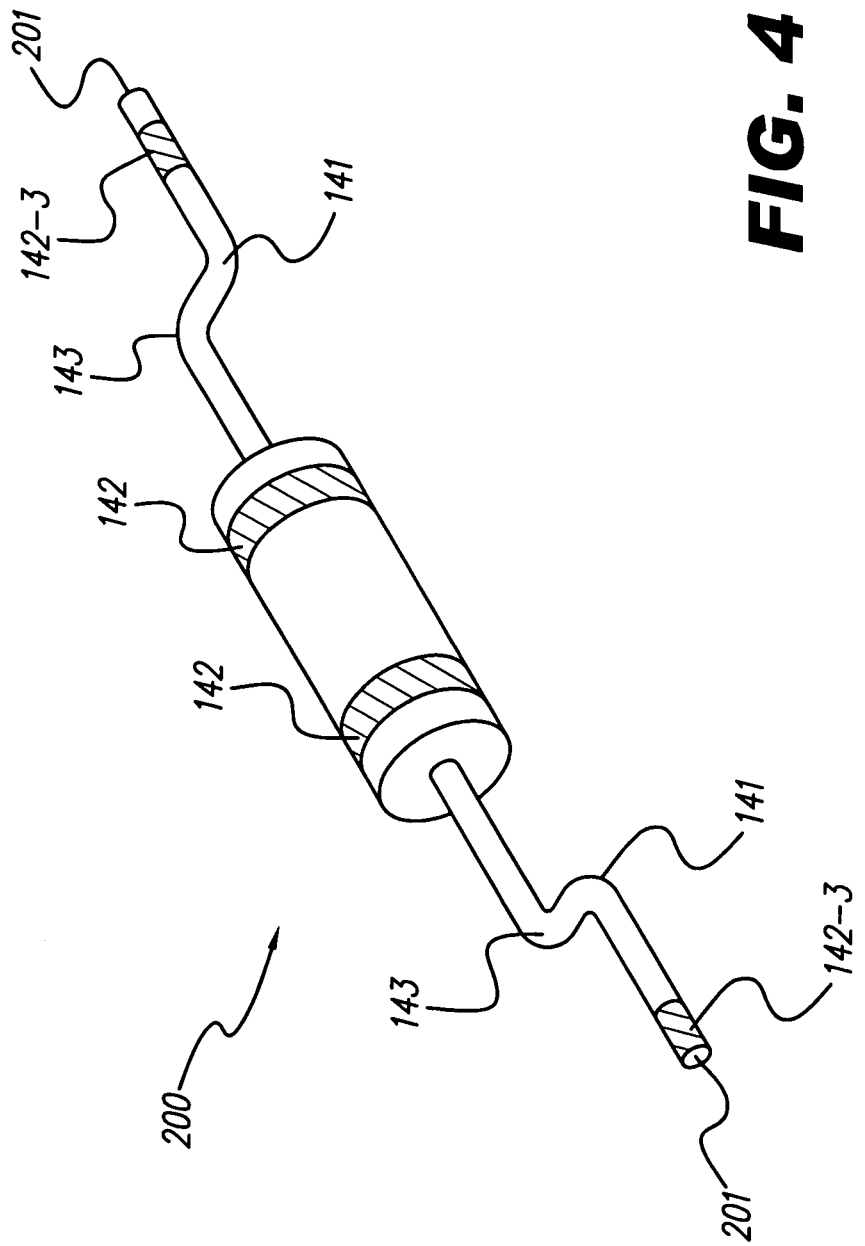
FIG. 4 shows one or more catheters coupled to a microstimulator according to principles described herein.

FIG. 4 shows an example of a microstimulator (200) with one or more catheters (143) coupled to the infusion outlets on the body of the microstimulator (200). With the catheters (143) in place, the infusion outlets (201) that actually deliver the drug therapy to target tissue are located at the ends of catheters (143). Thus, in the example of FIG. 4, a drug therapy is expelled by the pump (147, FIG. 3) from an infusion outlet (201, FIG. 3) in the casing (202, FIG. 3) of the microstimulator (200), through the catheter (143), out an infusion outlet (201) at the end of the catheter (143) to the stimulation site within the patient. As shown in FIG. 4, the catheters (143) may also serve as leads (141) having one or more electrodes (142-3) disposed thereon. Thus, the catheters (143) and leads (141) of FIG. 4 permit infused drugs and/or electrical stimulation current to be directed to a stimulation site while allowing most elements of the microstimulator (200) to be located in a more surgically convenient site. The example of FIG. 4 may also include leadless electrodes (142) disposed on the housing of the microstimulator (200), in the same manner described above.

Figure 5:
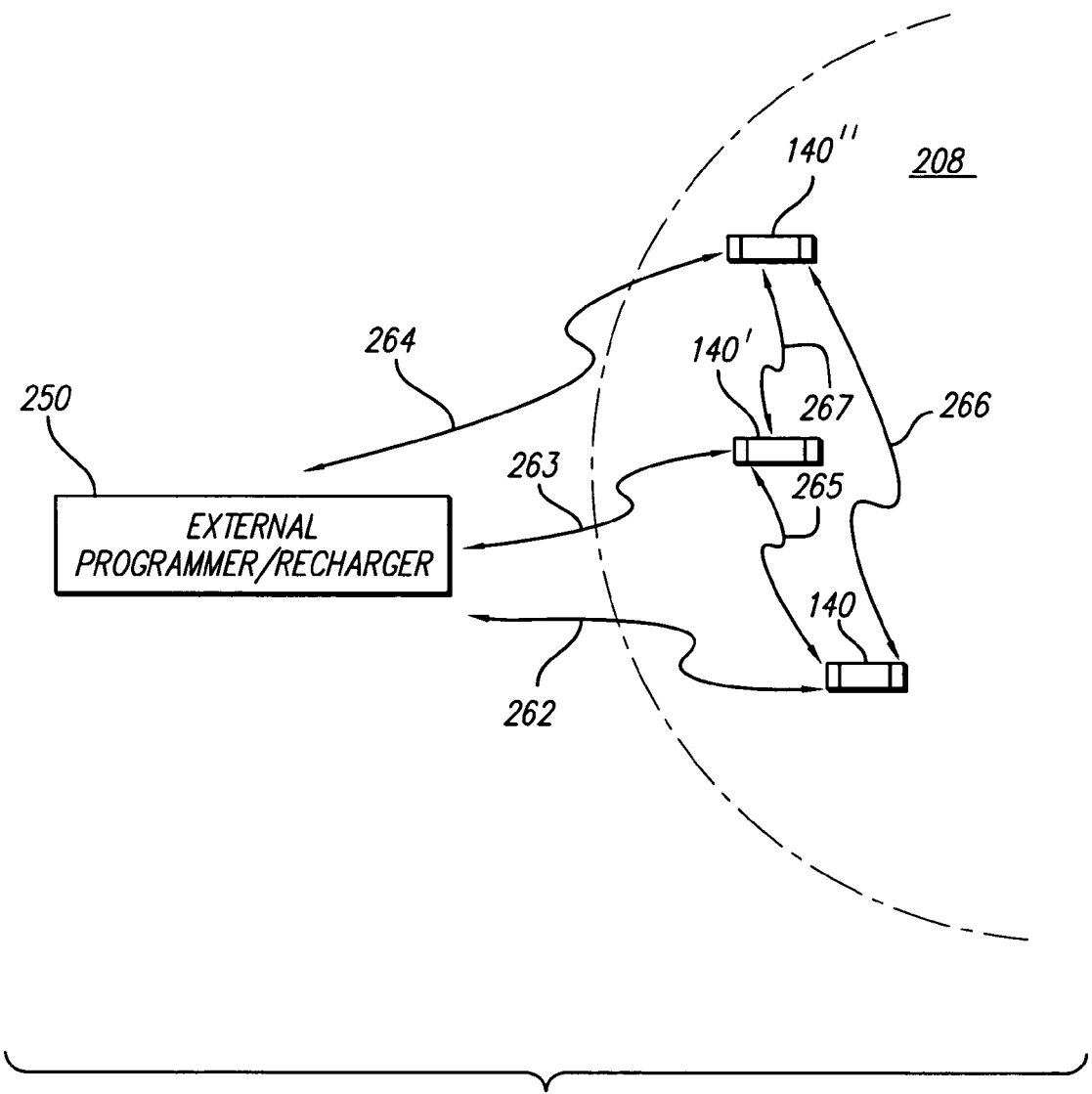
FIG. 5 depicts a number of stimulators configured to communicate with each other and/or with one or more external devices according to principles described herein.

Returning to FIG. 2, the stimulator (140) may be configured to operate independently. Alternatively, as shown in FIG. 5 and described in more detail below, the stimulator (140) may be configured to operate in a coordinated manner with one or more additional stimulators, other implanted devices, or other devices external to the patient's body. For instance, a first stimulator may control, or operate under the control of, a second stimulator, other implanted device, or other device external to the patient's body. The stimulator (140) may be configured to communicate with other implanted stimulators, other implanted devices, or other devices external to the patient's body via an RF link, an untrasonic link, an optical link, or any other type of communication link. For example, the stimulator (140) may be configured to communicate with an external remote control unit that is configured to send commands and/or data to the stimulator (140) and that is configured to receive commands and/or data from the stimulator (140).

In order to determine the strength and/or duration of electrical stimulation and/or amount and/or type(s) of stimulating drug(s) required to most effectively promote neural remodeling, various indicators of a medical condition and/or a patient's response to treatment may be sensed or measured. These indicators include, but are not limited to, electrical activity of the brain (e.g., EEG); neurotransmitter levels; hormone levels; metabolic activity in the brain; blood flow rate in the head, neck or other areas of the body; medication levels within the patient; patient or caregiver input, e.g., the stimulation may be in response to a physical manifestation of a medical condition; temperature of tissue at the stimulation site; and/or brain hyperexcitability, e.g., increased response of given tissue to the same input. In some embodiments, the stimulator (140) may be configured to adjust the stimulation parameters in a closed loop manner in response to these measurements. The stimulator (140) may be configured to perform the measurements. Alternatively, other sensing devices may be configured to perform the measurements and transmit the measured values to the stimulator (140). Exemplary sensing devices include, but are not limited to, chemical sensors, electrodes, optical sensors, mechanical (e.g., motion, pressure) sensors, and temperature sensors.

Thus, one or more external devices may be provided to interact with the stimulator (140), and may be used to accomplish at least one or more of the following functions:

Function 1: If necessary, transmit electrical power to the stimulator (140) in order to power the stimulator (140) and/or recharge the power source (145).

Function 2: Transmit data to the stimulator (140) in order to change the stimulation parameters used by the stimulator (140).

Function 3: Receive data indicating the state of the stimulator (140) (e.g., battery level, drug level, stimulation parameters, etc.).

Additional functions may include adjusting the stimulation parameters based on information sensed by the stimulator (140) or by other sensing devices.

By way of example, an exemplary method of promoting neural remodeling within a patient to treat a medical condition may be carried out according to the following sequence of procedures. The steps listed below may be modified, reordered, and/or added to as best serves a particular application.

1. A stimulator (140) is implanted so that its electrodes (142) and/or infusion outlet (149) are coupled to or located near a stimulation site within the brain. If the stimulator (140) is a microstimulator, such as the microstimulator (200) described in FIG. 3, the microstimulator itself may be coupled to the stimulation site.

2. The stimulator (140) is programmed to apply at least one stimulus to the stimulation site. The stimulus may include electrical stimulation, drug stimulation, gene infusion, chemical stimulation, thermal stimulation, electromagnetic stimulation, mechanical stimulation, and/or any other suitable stimulation.

3. When the patient desires to invoke stimulation, the patient sends a command to the stimulator (140) (e.g., via a remote control) such that the stimulator (140) delivers the prescribed stimulation. The stimulator (140) may additionally or alternatively be configured to automatically apply the stimulation in response to sensed indicators of the medical condition.

4. To cease stimulation, the stimulator (140) may be turned off (e.g., via a remote control).

5. Periodically, the power source (145) of the stimulator (140) is recharged, if necessary, in accordance with Function 1 described above.

In alternative examples, the treatment administered by the stimulator (140), i.e., drug therapy and/or electrical stimulation, may be automatic and not controlled or invoked by the patient. For example, the stimulator (140) may stimulate in a closed-loop manner in response to feedback from the body. Such feedback signals may include, but are not limited to, electrical activity of neural tissue (e.g., EEG), concentration of neurotransmitters, concentration of compounds related to metabolic rate (glucose, oxygen, etc), concentration of other the chemicals infused by the system or its metabolized components, and tissue impedance.

For the treatment of different patients, it may be desirable to modify or adjust the algorithmic functions performed by the implanted and/or external components, as well as the surgical approaches. For example, in some situations, it may be desirable to employ more than one stimulator (140), each of which could be separately controlled by means of a digital address. Multiple channels and/or multiple patterns of stimulation may thereby be used to deal with multiple medical conditions, such as, for example, the combination of autism with a seizure disorder.

As shown in the example of FIG. 5, a first stimulator (140) implanted beneath the skin of the patient (208) provides a stimulus to a first location; a second stimulator (140') provides a stimulus to a second location; and a third stimulator (140") provides a stimulus to a third location. As mentioned earlier, the implanted devices may operate independently or may operate in a coordinated manner with other implanted devices or other devices external to the patient's body. That is, an external controller (250) may be configured to control the operation of each of the implanted devices (140, 140', and 140"). In some embodiments, an implanted device, e.g. stimulator (140), may control, or operate under the control of, another implanted device(s), e.g. stimulator (140') and/or stimulator (140"). Control lines (262-267) have been drawn in FIG. 5 to illustrate that the external controller (250) may communicate or provide power to any of the implanted devices (140, 140', and 140") and that each of the various implanted devices (140, 140', and 140") may communicate with and, in some instances, control any of the other implanted devices.

As a further example of multiple stimulators (140) operating in a coordinated manner, the first and second stimulators (140, 140') of FIG. 5 may be configured to sense various indicators of a medical condition and transmit the measured information to the third stimulator (140"). The third stimulator (140") may then use the measured information to adjust its stimulation parameters and apply stimulation to a stimulation site accordingly. The various implanted stimulators may, in any combination, sense indicators of the medical condition, communicate or receive data on such indicators, and adjust stimulation parameters accordingly.

Alternatively, the external device (250) or other external devices communicating with the external device may be configured to sense various indicators of a patient's condition. The sensed indicators may then be collected by the external device (250) for relay to one or more of the implanted stimulators or may be transmitted directly to one or more of the implanted stimulators by any of an array of external sensing devices. In either case, the stimulator, upon receiving the sensed indicator(s), may adjust stimulation parameters accordingly. In other examples, the external controller (250) may determine whether any change to stimulation parameters is needed based on the sensed indicators. The external device (250) may then signal a command to one or more of the stimulators to adjust stimulation parameters accordingly.

The stimulator (140) of FIG. 2 may be implanted within a patient using any suitable surgical procedure such as, but not limited to, injection, small incision, open placement, laparoscopy, or endoscopy. Exemplary methods of implanting a microstimulator, for example, are described in U.S. Pat. Nos. 5,193,539; 5,193,540; 5,312,439; 6,185,452; 6,164,284; 6,208,894; and 6,051,017. Exemplary methods of implanting an SCS, for example, are described in U.S. Pat. Nos. 5,501, 703; 6,487,446; and 6,516,227. Exemplary methods of implanting a deep brain stimulator, for example, are described in U.S. Pat. Nos. 5,938,688; 6,016,449; and 6,539, 263. All of these listed patents are incorporated herein by reference in their respective entireties.

Figure 6:
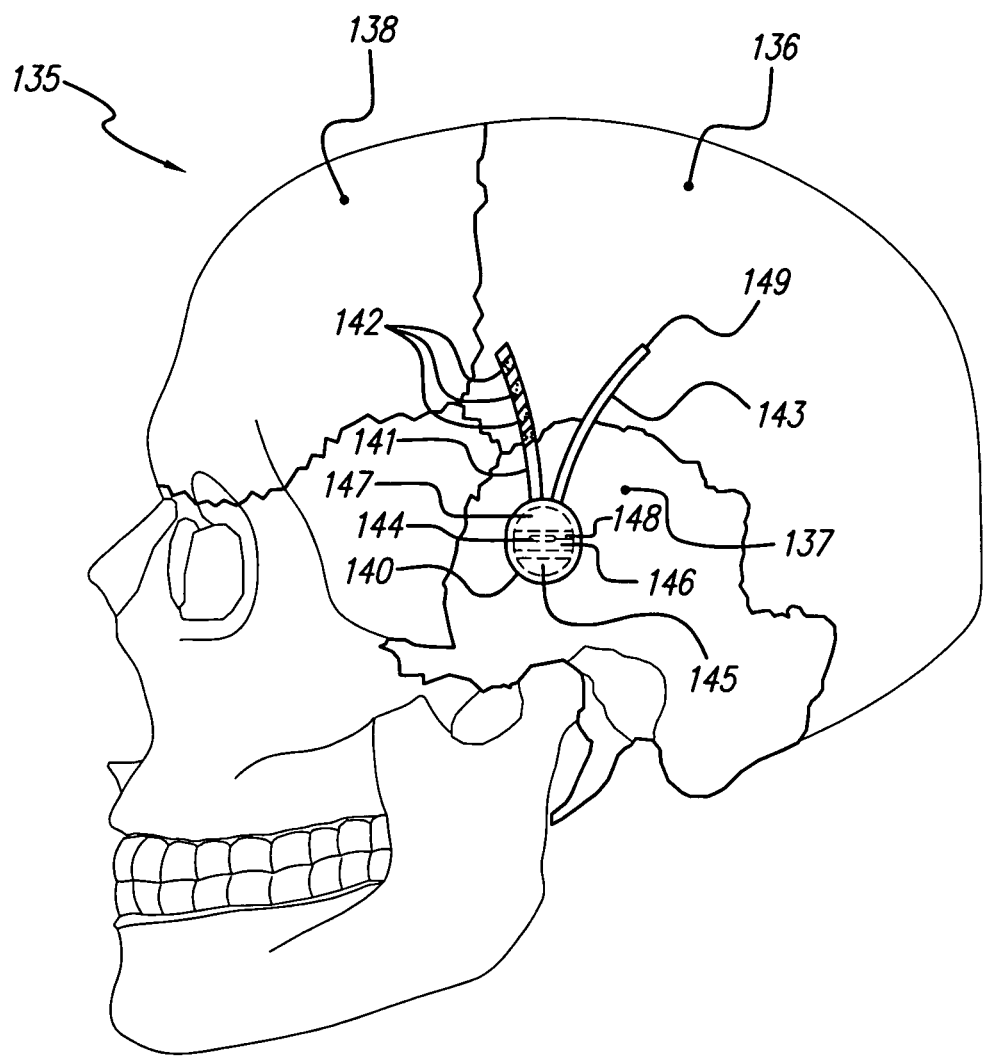
FIG. 6 illustrates a stimulator that has been implanted beneath the scalp of a patient to stimulate a stimulation site within the brain according to principles described herein.

By way of example, FIG. 6 shows a stimulator (140) (e.g., a deep brain stimulator) that has been implanted beneath the scalp of a patient to promote neural remodeling at a stimulation site within the brain. The stimulator (140) may be implanted in a surgically-created shallow depression or opening in the skull (135). For instance, the depression may be made in the parietal bone (136), temporal bone (137), frontal bone (138), or any other bone within the skull (135) as best serves a particular application. The stimulator (140) may conform to the profile of surrounding tissue(s) and/or bone(s), thereby minimizing the pressure applied to the skin or scalp. Additionally or alternatively, the stimulator (140) may be implanted in a subdural space over any of the lobes of the brain, in a sinus cavity, or in an intracerebral ventricle.

In some examples, as shown in FIG. 6, a lead (141) and/or catheter (143) may run subcutaneously to an opening in the skull (135) and pass through the opening into or onto a stimulation site in the brain. Alternatively, the stimulator (140) is leadless and is configured to generate a stimulus that passes through the skull. In this manner, the brain may be stimulated without having to physically invade the brain itself.

Figure 7:
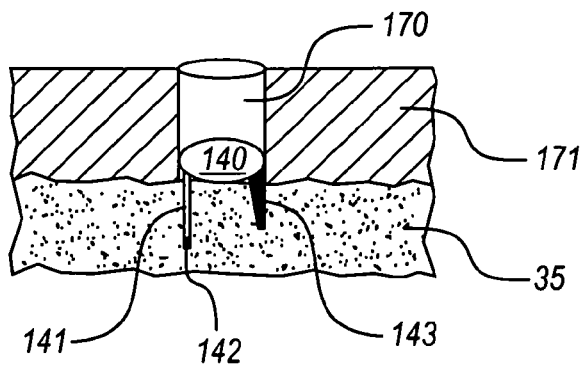
FIG. 7 is cross-sectional view of a stimulator implanted within a hole created in the skull of a patient according to principles described herein.

Alternatively, as shown in the cross-sectional view of FIG. 7, the stimulator (140) may be implanted within the lumen of a hole (170) created in the skull (171) and configured to apply a stimulus to a stimulation site within the brain (e.g., the cerebral cortex (35)). The hole (170) may be a burr hole, for example, and may be created with a surgical drill or any other suitable device. The hole (171) extends at least partially into the skull (171), and, as shown in FIG. 7, may extend all the way through the skull (171). The stimulator (140) is placed within the lumen of the hole (170) and coupled to the walls of the hole (170) and/or the top surface of the stimulation site, e.g., the cerebral cortex (35), using an adhesive, suture, or any other fastening device. Once the stimulator (140) has been implanted, the hole (170) may be covered by an appropriately sized cap (not shown).

As shown in FIG. 7, a lead (141) may be coupled to the stimulator (140) with the distal end of the lead (141) being routed to a particular location within the cerebral cortex (35) or other stimulation site in the brain. The distal end of the lead (141) may include one or more electrodes (142) configured to deliver an electrical stimulation current to the stimulation site. A catheter (143) may additionally or alternatively be coupled to the stimulator (140) and routed to the stimulation site so as to deliver one or more drugs at the stimulation site.

Figure 8A:
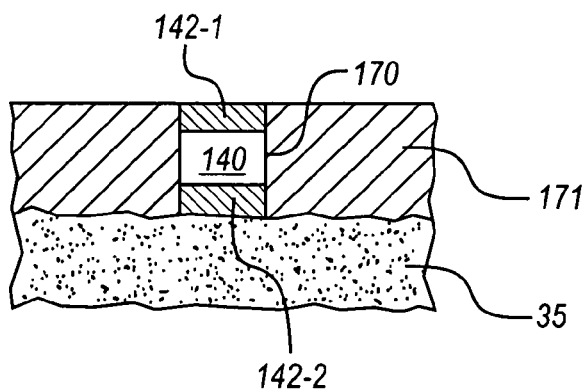
FIG. 8A is a cross-sectional view of a stimulator having two ring-like electrodes disposed on its surface implanted within a hole created in the skull of a patient according to principles described herein.
Figure 8B:
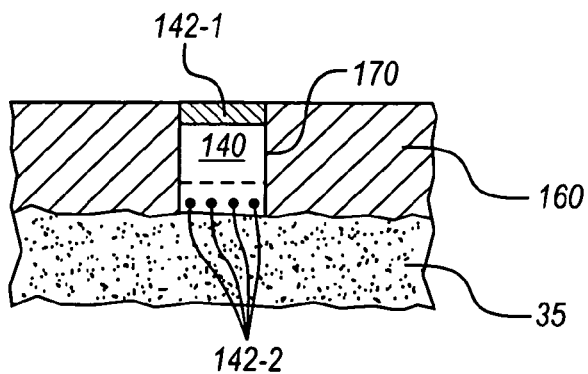
FIG. 8B is a cross-sectional view of a stimulator having multiple electrodes disposed thereon implanted within a hole created in the skull of a patient according to principles described herein.

As mentioned, the stimulator (140) may be leadless. FIGS. 8A-8B are cross sectional views of exemplary leadless stimulators (140) that have been implanted within the lumen of a hole (170) created in the skull (171). In this manner, the stimulation site within the brain may be stimulated without having to physically invade the brain itself.

For example, FIG. 8A shows an exemplary stimulator (140) with two ring-like electrodes (142) disposed on its surface. The electrode (142-2) more proximal to the stimulation site, e.g., the cerebral cortex (35), may be configured to act as a stimulating electrode while the electrode (142-2) more distal to the stimulation site may be configured to act as the indifferent electrode.

FIG. 8B shows an alternative electrode arrangement wherein the end closest to the stimulation site includes multiple electrodes (142-2) disposed thereon. Each electrode (142-2) may be selectively configured to act as either an anode or cathode so that monopolar and/or multipolar stimulation may be applied to the stimulation site. The distal end of the stimulator (140) may also include a selectively programmable electrode (142-1).

Figure 9:
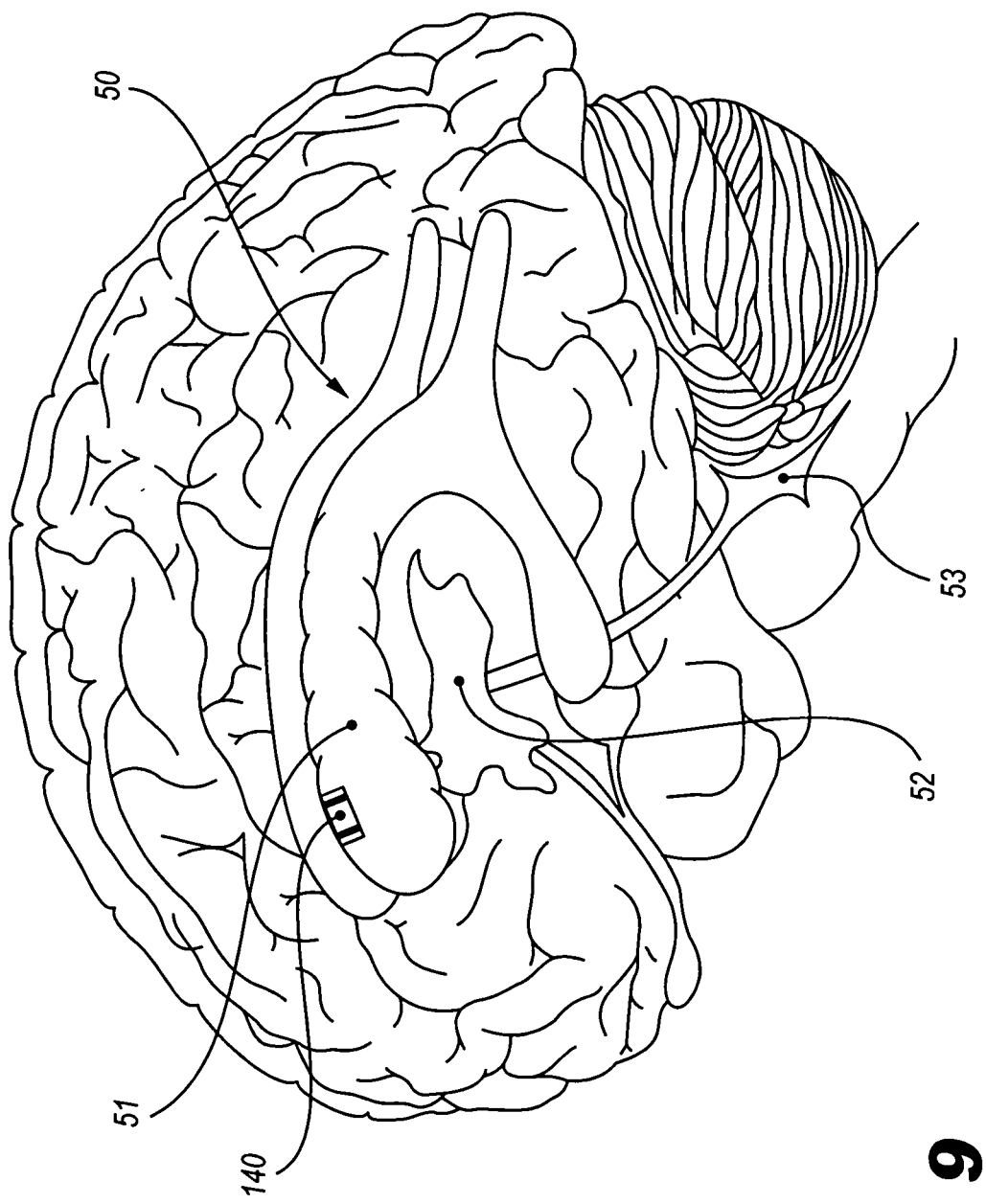
FIG. 9 illustrates an exemplary stimulator that has been implanted within a cerebral ventricle according to principles described herein.

In some examples, it is believed that neural remodeling may be promoted by applying the stimulus to the cerebrospinal fluid found within the cerebral ventricles. For example, one or more drugs may be infused into the cerebrospinal fluid. The cerebrospinal fluid may then transport the drugs to various locations throughout the brain to promote neural remodeling. To this end, the stimulator (140), stimulating lead (141), and/or catheter (143) may be implanted within one of the cerebral ventricles. For example, FIG. 9 illustrates an exemplary stimulator (140) that has been implanted within the lateral ventricle (51). The stimulator (140) may be coupled to one of the walls of the lateral ventricle (51) using any suitable fixation device (e.g., sutures, adhesives, hooks, or barbs). Alternatively, the stimulator (140) is implanted in a more distal location (e.g., within the sinus cavity or chest) and coupled to a lead and/or catheter that extends into one of the cerebral ventricles.

In some examples, it may be desired to promote neural remodeling at a particular location or region within the brain while not affecting other locations within the brain. To this end, the stimulation may be localized such that it only affects the desired location. For example, the stimulation may be configured to induce focal epileptiform activity at the desired location such that neural remodeling occurs only at the desired location.

As mentioned, it is believed that the stimulation provided by the stimulator (140) may be configured to induce neural dedifferentiation at a particular location or region within the brain. In other words, the stimulation may be configured to induce a number of neurons at that location to break already formed synaptic contacts and revert to a more juvenile phenotype. It is believed that the affected portion of the brain may then follow normal developmental patterns to reestablish correct and/or more efficient neural connections. These developmental patterns are similar to those followed in processes involved in learning.

It will be recognized that the synaptic contacts may be broken using any suitable method or technique. In some examples, synaptic connections may be broken by affecting the normal feedback loops that maintain them, changing the concentration of ions therein, preventing neuronal firing, and/or modifying neurotransmitter concentration. One such mechanism involve silencing pre-synaptic neurons to prevent them from releasing neurotransmitters. Similarly, a post-synaptic neuron may be prevented from acting on a pre-synaptic signal by releasing substances that have the opposite effect of the pre-synaptic neuron, using post-synaptic depolarizing agents, using receptor blockers, or by exciting other neurons.

Another method of breaking synaptic connections includes increasing the strength of the connections of surrounding neurons. This will in effect reduce the relative weight of the undesired pre-synaptic neuron. The increased activity of other neurons may then mask or filter the activity of the offending synapse.

Once the neurons have dedifferentiated, the stimulation provided by the stimulator (140) may be adjusted to assist in the reestablishment of correct neural connections (i.e., redifferentiation). Exemplary drugs that may be applied to the brain to assist in the reestablishment of neural connections include, but are not limited to, neurotrophic factors, fibroblast growth factors, ethanol, and steroid hormones. Each of these drugs promote cell growth and/or cell division. For example, fibroblast growth factors are proteins that bind to receptors on the cell surface, with the primary result of activating cellular proliferation and/or differentiation. Many growth factors are quite versatile, stimulating cellular division in numerous different cell types.

Additionally or alternatively, the stimulation provided by the stimulator (140) may be configured to disrupt the long-term potentiation (LTP), i.e., the existing structure, of synaptic connections in order to promote neural remodeling. LTP refers to the ability of neural connections to strengthen and become more established over time. The biological mechanisms of LTP, largely through the interplay of protein kinases, phosphatases, and gene expression, give rise to synaptic plasticity (i.e., the ability of a synaptic connection between two neurons to change in strength). Hence, by disrupting established LTP, changes in neural structures may be ameliorated and/or new LTP at more appropriate synapses may be facilitated.

In some examples, the stimulus applied by the stimulator (140) includes electroconvulsive therapy and/or pentylenetetrazol injections. These types of stimulation cause global seizure activity (e.g., focal epileptiform activity), which in turn promotes neural remodeling. The electroconvulsive therapy may additionally or alternatively be applied by paddles on the surface of the cerebral cortex.

As mentioned, neural remodeling may be effective in treating brain injuries. In a stroke, for example, neurons within portions of the brain that are deprived of oxygen may die. The functions served by these neurons are then detrimentally affected. If, however, developmental plasticity could be reestablished at the time of the stroke, the remaining portions of the brain may be able to take over for the damaged area and allow recovery of function.

It will be recognized that the stimulation applied by the stimulator (140) may be combined with any other type of treatment to promote neural remodeling. For example, sleep deprivation or the prevention of rapid eye movement (REM) sleep may be used in combination with the application of one or more stimuli to the brain to promote neural remodeling.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of treating a medical condition of a patient, said method comprising:
    generating an electrical stimulus in accordance with one or more stimulation parameters and
    applying said electrical stimulus to a stimulation site of a brain of said patient to decrease the relative excitement between neurons that are the source of said medical condition and neural tissue surrounding said neurons, thereby inducing said neurons to break synaptic contacts and revert to a juvenile phenotype.

2. The method of claim 1, further comprising sensing at least one indicator related to said medical condition and using said at least one sensed indicator to adjust said one or more stimulation parameters.

3. The method of claim 2, wherein said at least one indicator comprises at least one or more of an electrical activity of said brain, a chemical level of said brain, a neurotransmitter level, a hormone level, and a medication level.

4. The method of claim 1, wherein said stimulation site comprises at least one or more of a temporal lobe, cerebral ventricle, structure within a limbic system, pituitary gland, brainstem, and cerebral cortex.

5. The method of claim 1, wherein said medical condition comprises at least one or more of autism, a psychological disorder, a neurodegenerative disease, a chromosomal abnormality, a bad habit, and an injury to said brain.

6. The method of claim 1, further comprising:
    adjusting said one or more stimulation parameters;
    generating another electrical stimulus in accordance with said adjusted one or more stimulation parameters;
    applying said other electrical stimulus to said one or more neurons to facilitate redifferentiation of said one or more neurons.

7. The method of claim 1, wherein said one or more stimulation parameters comprises a frequency greater than 100 Hz.

8. The method of claim 1, wherein said stimulation site includes said neurons, wherein excitement of the neurons is decreased by the application of said electrical stimulus.

9. The method of claim 1, wherein said stimulation site includes said surrounding neural tissue, wherein the strength of the connection of neurons within said neural tissue is strengthened.

* * * * *